United States Patent [19]
Wilson, Jr.

[11] Patent Number: 6,096,677
[45] Date of Patent: Aug. 1, 2000

[54] SUPPORTED METALLOCENE CATALYSTS

[75] Inventor: Robert B. Wilson, Jr., Palo Alto, Calif.

[73] Assignee: SRI International, Menlo Park, Calif.

[21] Appl. No.: 09/247,662

[22] Filed: Feb. 9, 1999

Related U.S. Application Data

[62] Division of application No. 08/951,959, Oct. 17, 1997, Pat. No. 5,892,079.

[51] Int. Cl.$^7$ .............................. C07F 17/00; B01J 31/00; C08F 4/64

[52] U.S. Cl. .................... 502/120; 502/103; 502/117; 526/127; 526/160; 526/943; 534/11; 534/15; 556/1; 556/11; 556/12; 556/28; 556/43; 556/53

[58] Field of Search ................ 556/11, 12, 28, 556/43, 53, 1; 534/11, 15; 526/127, 160, 943; 502/103, 117, 120

[56] References Cited

U.S. PATENT DOCUMENTS

| | | | |
|---|---|---|---|
| 4,659,685 | 4/1987 | Coleman, III et al. | 502/113 |
| 5,032,562 | 7/1991 | Lo et al. | 502/111 |
| 5,055,438 | 10/1991 | Canich | 502/117 |
| 5,439,994 | 8/1995 | Inoue et al. | 526/114 |
| 5,442,020 | 8/1995 | Davis et al. | 526/127 |
| 5,525,678 | 6/1996 | Mink et al. | 523/246 |
| 5,585,508 | 12/1996 | Kuber et al. | 556/11 |
| 5,594,080 | 1/1997 | Waymouth et al. | 526/126 |
| 5,627,117 | 5/1997 | Mukaiyama et al. | 502/113 |
| 5,693,730 | 12/1997 | Küber et al. | 526/127 |
| 5,703,187 | 12/1997 | Timmers | 526/282 |

FOREIGN PATENT DOCUMENTS

| | | |
|---|---|---|
| 416815 A2 | 3/1991 | European Pat. Off. |
| 0528041A1 | 2/1993 | European Pat. Off. |
| 0632063A1 | 1/1995 | European Pat. Off. |
| 0 654 476 A1 | 5/1995 | European Pat. Off. |
| 0 739 897 A1 | 10/1996 | European Pat. Off. |
| 0 742 225 A1 | 11/1996 | European Pat. Off. |
| 0 779 295 A1 | 6/1997 | European Pat. Off. |
| 0 779 306 A2 | 6/1997 | European Pat. Off. |
| WO92/00333 | 1/1992 | WIPO |

OTHER PUBLICATIONS

A.D. Horton (1994), "Metallocene Catalysis: Polymers by Design," *Trends Polym. Sci.* 2(5):158–166.

Hüttenhofer et al. (1996), "Substituted Silastannatetrahydro–s–indacenes as Cyclopentadienyl Transfer Agents in the Synthesis of Silanediyl–Bridged Zirconocene Complexes," *Organometallics* 15:4816–4822.

Katayama et al. (1995), "The Effect of Aluminium Compounds in the Copolymerization of Ethylene/α–Olefins," in *Macromol.Symp.* 97:109–118.

Ushioda et al. (1996), "Synthesis and Catalytic Properties of Ansa–Binuclear Metallocenes of the Group IV Transition Metals," *Journal of Organometallic Chemistry*, 518:155–166.

Primary Examiner—Porfirio Nazario-Gonzalez
Attorney, Agent, or Firm—Dianne E. Reed; Reed & Associates

[57] ABSTRACT

Novel metallocene compounds are provided which are useful as polymerization catalysts, particularly in the polymerization of addition polymerizable monomers such as olefinic or vinyl monomers. Preferred polymer compositions prepared using the novel catalysts are bimodal or multimodal in nature, typically having a bimodal or multimodal molecular weight distribution. The metallocenes are binuclear or multinuclear, and contain two or more chemically distinct active sites. Methods for synthesizing the novel catalysts are also provided, as are methods for using the novel compounds as homogeneous or heterogeneous polymerization catalysts.

60 Claims, 1 Drawing Sheet

SUPPORTED METALLOCENE CATALYSTS

CROSS-REFERENCE TO RELATED APPLICATIONS

This is a divisional of U.S. patent application Ser. No. 08/951,959, filed Oct. 17, 1997 now U.S. Pat. No. 5,892,079.

TECHNICAL FIELD

This invention relates generally to the field of catalysis, and more particularly relates to novel metallocenes useful as polymerization catalysts. The invention additionally relates to methods of synthesizing the novel catalysts and to methods for using them in the preparation of polymers, particularly polyolefins.

BACKGROUND

Many processes and catalysts are known for the preparation of homopolymeric or copolymeric olefins and other polymers. Ziegler-Natta catalyst compositions, developed in the 1950s, were found to be particularly useful in the preparation of polyolefins. These catalyst compositions comprise transition metal compounds such as titanium tetrachloride and an alkylaluminum (e.g., triethylaluminum) cocatalyst. The systems were found to be advantageous because of their high activity, and were largely consumed during polymerization.

More recent catalyst systems for use in preparing polyolefins and other polymers are "metallocenes." The term "metallocene" was initially coined in the early 1950s to refer to dicyclopentadienyliron, or "ferrocene," a structure in which an iron atom is contained between and associated with two parallel cyclopentadienyl groups. The term is now used to refer generally to organometallic complexes in which a metal atom (not necessarily iron) is coordinated to at least one cyclopentadienyl ring ligand.

In contrast to the traditional Ziegler-Natta catalysts, metallocenes can provide a polymer composition containing a plurality of polymer molecules of substantially the same molecular structure. That is, if one high purity metallocene catalyst is used, the variance in the composition or molecular weight of the individual polymer molecules produced is minimal. With metallocenes, then, it is possible to control compositional distribution and other aspects of polymer molecular structure with unprecedented precision. Metallocene catalysts have other advantages as well. For example, metallocenes: (a) can polymerize almost any vinyl monomer irrespective of molecular weight or steric considerations; (b) provide the ability to control vinyl unsaturation in the polymers produced; (c) enable polymerization of a-olefins with very high stereoregularity to give isotactic or syndiotactic polymers; and (d) can function as hydrogenation catalysts for polymers as well as monomers. A. D. Horton, "Metallocene Catalysis: Polymers by Design," *Trends Polym. Sci.* 2(5):158–166 (1994), provides an overview of metallocene catalysts and their advantages, and focuses on now-conventional complexes of Group IV transition metal complexes and cyclopentadienyl ligands ($Cp_2MX_2$, wherein Cp represents a cyclopentadienyl ligand, M is Zr, Hf or Ti, and X is Cl or $CH_3$).

Horton, supra, discusses the utility of "uniform site" metallocene catalysts relative to traditional "multi-site" Ziegler-Natta polymerization catalysts, and emphasizes the ability to control polymer structure and properties by simply varying the catalyst structure. The catalysts proposed by Horton are homogeneous in nature, in contrast to the typically heterogeneous catalysts used in the preparation of polyolefins.

In addition, certain types of metallocene catalysts have been used to produce polymer compositions that are bimodal (or "bimolecular") or multimodal (or "multimolecular"). A composition referred to as "modal" or "multimodal" is generally, although not necessarily, bimodal or multimodal with respect to molecular weight distribution, i.e., the composition has two or more different molecular weight distributions, as may be determined, for example, by the appearance of two or more peaks in a gel permeation chromatogram. However, bimodality or multimodality can refer to other characteristics of a polymer composition as well, e.g., compositional distribution (the distribution of comonomers within a copolymer), tacticity distribution (wherein a polymer contains at least two segments of differing tacticity, long-chain branching distribution, or the like. Polymeric compositions that are multimodal are frequently more useful than compositions that are not; for example, multimodal polymer compositions can have improved rheological behavior, higher mechanical strength and increased elasticity relative to corresponding compositions which are not multimodal.

U.S. Pat. No. 5,525,678 to Mink et al. provides a supported catalyst composition for producing a polyolefin resin having a high molecular weight component and a low molecular weight component, wherein the catalyst composition contains a first catalyst which is a metallocene and a second catalyst which is a non-metallocene. The ratio of the high molecular weight and low molecular weight components in the polymeric product is determined by the ratio of the concentration of the two metals in the two-component catalyst composition. In addition, U.S. Pat. No. 4,659,685 to Coleman, III et al. pertains to a two-component catalyst composition for preparing polyolefins having a molecular weight distribution which is multimodal, the catalyst composition comprising a mixture of a supported titanium compound and a separately supported or non-supported organometallic compound.

U.S. Pat. No. 5,032,562 to Lo et al. also relates to a supported olefin polymerization catalyst composition for producing high density polyethylene ("HDPE") having a multimodal molecular weight distribution. The catalyst composition comprises: (1) a catalyst precursor supported on a porous carrier, and (2) a catalyst activator in the form of a mixture of conventional Ziegler-Natta cocatalysts. Katayama et al., "The Effect of Aluminium Compounds in the Copolymerization of Ethylene/α-Olefins," in *Macromol. Symp.* 97:109–118 (1995), provides a similar system for preparing a polymer composition having a bimodal composition using a two-component catalyst comprised of a metallocene ($Cp_2ZrCL_2$) and either $[Ph_3C^+][B(C_6F_5)_4^-]$ or $[PhMe_2NH^+][B(C_6F_5)_4^-,]$.

PCT Publication No. WO92/00333, inventors Canich et al., and EP 416,815 A2, inventors Stevens et al., are also of interest insofar as the references describe metallocene catalysts for preparing polyolefins. Canich et al. describes metallocene catalyst compositions for producing high molecular weight polyolefins having a relatively narrow molecular weight distribution, wherein the catalyst composition is comprised of (1) a metallocene containing a Group IVB transition metal coordinated to a cyclopentadienyl ligand, and (2) a coordination complex such as an anionic complex containing a plurality of boron atoms, which serves as a catalyst activator. The metallocene catalysts described may be mononuclear or binuclear (i.e., containing one or two metal atoms which serve as the active sites); the binuclear compounds dissociate during polymerization. Stevens et al. also pertains to metallocene catalysts to prepare addition polymers, particularly homopolymers and copolymers of olefins, diolefins, "hindered" aliphatic vinyl monomers and vinylidene aromatic monomers. The Stevens et al. catalysts are metal coordination complexes having constrained geometry, and are used in conjunction with a cocatalyst compound or composition to form a complete catalytic system. The constrained geometry of the catalysts is stated to be of key importance insofar as the metal atom in the metallocene presumably is a more "exposed" active site.

Thus, the art provides metallocene catalyst compositions for producing polymers, particular polyolefins, which have a bimodal or multimodal molecular weight distribution. However, prior catalysts and catalyst compositions, as described above, either require two or more components, e.g., two catalysts used in combination, or involve binuclear compounds which break apart into two separate components during the polymerization process (as in the bimetallic catalyst disclosed by Canich et al.), giving rise to potential manufacturing problems, e.g., phase separation or the like, and/or loss of control over the molecular weight distribution of the polymer composition prepared. In addition, the known metallocene catalysts can be relatively difficult and time-consuming to synthesize, requiring expensive equipment, extreme reaction conditions, and multi-step processes which ultimately result in a low yield of the desired product.

Accordingly, there is a need in the art for a simpler polymerization catalyst which does not require a second catalyst, retains its structure during the polymerization process, and is relatively simple to synthesize. The novel metallocene compounds of the invention address the aforementioned need in the art and represent a significant advance in the field of catalysis. The compounds are binuclear or multinuclear metallocenes, preferably although not necessarily containing two or more distinct and chemically different active sites, and can be used in a variety of contexts. A preferred use is in the production of polymer compositions that are bimodal or multimodal in nature, typically, although not necessarily, having a desired bimodal or multimodal weight distribution. The catalysts allow for a high degree of control over both the compositional distribution and molecular weight distribution of the final polymer composition, and provide for all of the advantages typically associated with metallocene catalysts, i.e., versatility and use in conjunction with a variety of monomer types, the ability to control the degree of vinyl unsaturation in the polymeric product, the capability of providing isotactic or syndiotactic polymers, and the like. In addition to their utility as polymerization catalysts, the novel metallocenes are also useful in catalyzing hydrogenation. The novel compounds may be supported or used as homogeneous catalysts.

SUMMARY OF THE INVENTION

Accordingly, it is a primary object of the invention to provide novel metallocene compounds useful as polymerization and/or hydrogenation catalysts.

It is another object of the invention to provide such compounds which are binuclear or multinuclear metallocenes useful as homogeneous or heterogeneous catalysts.

It is still another object of the invention to provide such compounds which are useful for preparing polyolefins or other polymers deriving from the polymerization of addition polymerizable monomers containing one or more degrees of unsaturation.

It is an additional object of the invention to provide such compounds which are useful for providing polymer compositions that are bimodal or multimodal in nature.

It is yet another object of the invention to provide such compounds which are useful for providing polymer compositions having a bimodal or multimodal molecular weight distribution.

It is a further object of the invention to provide methods for synthesizing the novel polymerization catalysts.

It is still a further object of the invention to provide methods for using the novel catalysts to prepare polyolefins or other polymers deriving from the polymerization of addition polymerizable monomers containing one or more degrees of unsaturation.

It is yet a further object of the invention to provide methods of using the novel catalysts to prepare polymers deriving from the polymerization of aromatic monomers such as styrene, indene, or the like, or from the polymerization of esters, silanes, boranes or other reactive monomers.

Additional objects, advantages and novel features of the invention will be set forth in part in the description which follows, and in part will become apparent to those skilled in the art upon examination of the following, or may be learned by practice of the invention.

The novel metallocene catalysts have the structure $B(Z)_q$ as shown in Formula (I)

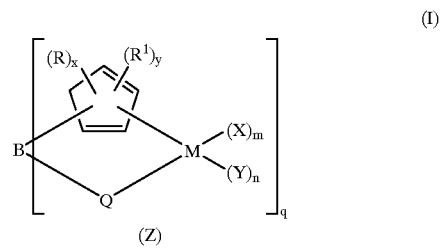

wherein:

B is a covalent bridging group comprising a $C_1$–$C_{24}$ hydrocarbyl radical optionally containing a Group IVB element, a Group VB element, or both a Group IVB element and a Group VB element, and is capable of binding up to $n_{max}$ substituents through single covalent bonds;

R and $R^1$ are independently selected from the group consisting of halogen, $C_1$–$C_{24}$ hydrocarbyl, $C_1$–$C_{24}$ hydrocarbyl substituted with one or more halogen atoms, and $C_1$–$C_{24}$ hydrocarbyl-substituted Group IVB elements, x is 0, 1, 2, 3 or 4, and y is 0, 1, 2, 3 or 4, with the proviso that the sum of x and y cannot exceed 4, or, when R and $R^1$ are ortho to each other and x and y are each 1 or greater, R and $R^1$ they can together form a five- or six-membered cyclic structure optionally substituted with one to four substituents selected from the group consisting of halogen, $C_1$–$C_{24}$ hydrocarbyl, $C_1$–$C_{24}$ hydrocarbyl substituted with one or more halogen atoms, and $C_1$–$C_{24}$ hydrocarbyl-substituted Group IVB elements;

Q is cyclopentadienyl, indenyl, fluorenyl, indolyl or aminoboratobenzyl, optionally substituted with one or more R and $R^1$ substituents as above, or Q is $J(R^2)_{z-2}$ wherein J is an element with a coordination number of three from Group VB or an element with a coordination number of two from Group VIB, $R^2$ is selected from the group consisting of hydrogen, $C_1$–$C_{24}$ hydrocarbyl, $C_1$–$C_{24}$ hydrocarbyl substituted with one or more halogen atoms, and $C_1$–$C_{24}$ alkoxy, and z is the coordination number of J, and further wherein Q substituents on different Z groups may be linked through a $C_1$–$C_{24}$ hydrocarbylene bridge;

M is a Group IIIA element, a Group IVA element, a Group VA lanthanide, or an actinide;

X is selected from the group consisting of hydride, halide, alkoxy, amido, $C_1$–$C_{24}$ hydrocarbyl, $C_1$–$C_{24}$ hydrocarbyl radicals substituted with one or more electron-withdrawing groups, and $C_1$–$C_{24}$ hydrocarbyl-substituted Group IVB elements, or, when two or more X substituents are present, they may together form an alkylidene olefin, acetylene, or a five- or six-membered cyclic hydrocarbyl group;

Y is a neutral Lewis base;

m is 1, 2, 3 or 4, and n is 0, 1, 2 or 3, with the proviso that if M is a Group IIIA element, m is 1 and n is 0, and with the further proviso that if M is a Group IVB element, the sum of m and n does not exceed 2;

q is an integer in the range of 2 to $q_{max}$, wherein $q_{max}$ is equal to $\frac{1}{2}n_{max}$ when $n_{max}$ is an even number, and $\frac{1}{2}(n_{max}^-)$ when $n_{max}$ is an odd number, with the proviso that when q is 2 and the M's in different Z groups are the same, Q is necessarily $J(R^2)_{z-2}$; and the Z substituents bound to B may be the same or different.

The catalyst may be supported or unsupported; if supported, conventional inert inorganic support materials are used, e.g., oxides of silicon, aluminum or the like. Typically, polymerization involves conventional processes wherein selected monomers are contacted with the novel catalyst under reaction conditions effective to provide the desired polymer composition. Polymerization may be carried out in solution, in a slurry, or in the gas phase.

DETAILED DESCRIPTION OF THE INVENTION

Figure 1:
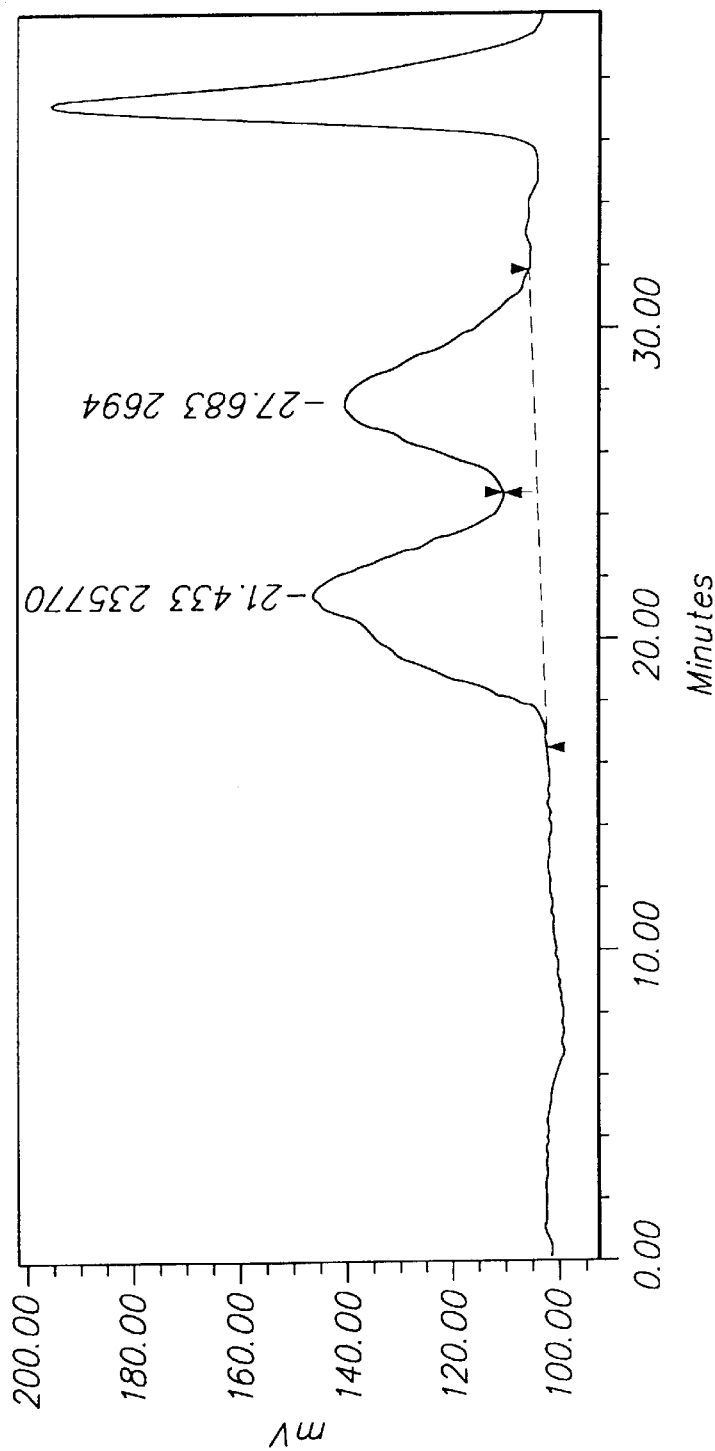
FIG. 1 is a gel permeation chromatogram for a polymer composition prepared using a binuclear metallocene catalyst of the invention.

Definitions and Nomenclature:

Before the present compounds, compositions and methods are disclosed and described, it is to be understood that this invention is not limited to specific molecular structures, ligands, or the like, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an electron-withdrawing group" as in a moiety "substituted with an electron-withdrawing group" includes more than one electron-withdrawing group, such that the moiety may be substituted with two or more such groups. Similarly, reference to "a halogen atom" as in a moiety "substituted with a halogen atom" includes more than one halogen atom, such that the moiety may be substituted with two or more halogen atoms, reference to "a substituent" includes one or more substituents, reference to "a ligand" includes one or more ligands, and the like.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. The term "lower alkyl" intends an alkyl group of 1 to 6 carbon atoms, preferably 1 to 4 carbon atoms.

The term "alkylene" as used herein refers to a difunctional saturated branched or unbranched hydrocarbon chain containing from 1 to 24 carbon atoms, and includes, for example, methylene (—$CH_2$—), ethylene (—$CH_2$—$CH_2$—), propylene (—$CH_2$—$CH_2$—$CH_2$—), 2-methyl-propylene (—$CH_2$—CH($CH_3$)—$CH_2$—), hexylene (—$(CH)_6$—), and the like. "Lower alkylene" refers to an alkylene group of 1 to 6, more preferably 1 to 4, carbon atoms.

The term "alkenyl" as used herein refers to a branched or unbranched hydrocarbon group of 2 to 24 carbon atoms containing at least one carbon-carbon double bond, such as ethenyl, n-propenyl, isopropenyl, n-butenyl, isobutenyl, t-butenyl, octenyl, decenyl, tetradecenyl, hexadecenyl, eicosenyl, tetracosenyl and the like. Preferred alkenyl groups herein contain 2 to 12 carbon atoms and 2 to 3 carbon-carbon double bonds. The term "lower alkenyl" intends an alkenyl group of 2 to 6 carbon atoms, preferably 2 to 4 carbon atoms, containing one —C=C— bond. The term "cycloalkenyl" intends a cyclic alkenyl group of 3 to 8, preferably 5 or 6, carbon atoms.

The term "alkenylene" refers to a difunctional branched or unbranched hydrocarbon chain containing from 2 to 24 carbon atoms and at least one carbon-carbon double bond. "Lower alkenylene" refers to an alkenylene group of 2 to 6, more preferably 2 to 5, carbon atoms, containing one —C=C— bond.

The term "alkynyl" as used herein refers to a branched or unbranched hydrocarbon group of 2 to 24 carbon atoms containing at least one —C≡C— bond, such as ethynyl, n-propynyl, isopropynyl, n-butynyl, isobutynyl, t-butynyl, octynyl, decynyl and the like. Preferred alkynyl groups herein contain 2 to 12 carbon atoms. The term "lower alkynyl" intends an alkynyl group of 2 to 6, preferably 2 to 4, carbon atoms, and one —C≡C— bond.

The term "alkynylene" refers to a difunctional branched or unbranched hydrocarbon chain containing from 2 to 24 carbon atoms and at least one carbon-carbon triple bond. "Lower alkynylene" refers to an alkynylene group of 2 to 6, more preferably 2 to 5, carbon atoms, containing one —C≡C— bond.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing one to six, more preferably one to four, carbon atoms.

The term "aryl" as used herein refers to an aromatic species containing 1 to 5 aromatic rings, either fused or linked, and either unsubstituted or substituted with 1 or more substituents typically selected from the group consisting of —$(CH_2)_x$—$NH_2$, —$(CH_2)$, —COOH, —$NO_2$, halogen and lower alkyl, where x is an integer in the range of 0 to 6 inclusive as outlined above. Preferred aryl substituents contain 1 to 3 fused aromatic rings, and particularly preferred aryl substituents contain 1 aromatic ring or 2 fused aromatic rings. The term "aralkyl" intends a moiety containing both alkyl and aryl species, typically containing less than about 24 carbon atoms, and more typically less than about 12 carbon atoms in the alkyl segment of the moiety, and typically containing 1 to 5 aromatic rings. The term "aralkyl" will usually be used to refer to aryl-substituted alkyl groups. The term "aralkylene" will be used in a similar manner to refer to moieties containing both alkylene and aryl species, typically containing less than about 24 carbon atoms in the alkylene portion and 1 to 5 aromatic rings in the aryl portion, and typically aryl-substituted alkylene. Exemplary aralkyl groups have the structure —$(CH_2)_j$—Ar wherein j is an integer in the range of 1 to 24, more typically 1 to 6, and Ar is a monocyclic aryl moiety.

The term "arylene" refers to a difunctional aromatic moiety; "monocyclic arylene" refers to a cyclopentylene or phenylene group. These groups may be substituted with up to four ring substituents as outlined above.

The term "heterocyclic" refers to a five- or six-membered monocyclic structure or to an eight- to eleven-membered bicyclic structure which is either saturated or unsaturated. Each heterocycle consists of carbon atoms and from one to four heteroatoms selected from the group consisting of nitrogen, oxygen and sulfur. As used herein, the terms "nitrogen heteroatoms" and "sulfur heteroatoms" include any oxidized form of nitrogen and sulfur, and the quaternized form of any basic nitrogen. Examples of heterocyclic groups include piperidinyl, morpholinyl and pyrrolidinyl.

"Halo" or "halogen" refers to fluoro, chloro, bromo or iodo, and usually relates to halo substitution for a hydrogen atom in an organic compound. Of the halos, chloro and fluoro are generally preferred.

"Hydrocarbyl" refers to unsubstituted and substituted hydrocarbyl radicals containing 1 to about 20 carbon atoms, including branched or unbranched, saturated or unsaturated species, such as alkyl groups, alkenyl groups, aryl groups, and the like. The term "lower hydrocarbyl" intends a hydrocarbyl group of one to six carbon atoms, preferably one to four carbon atoms. "Cyclometallated hydrocarbyl" refers to a cyclic hydrocarbyl group containing one or more metal atoms, typically a single metal atom.

"Optional" or "optionally" means that the subsequently described event or circumstance may or may not occur, and that the description includes instances where said event or circumstance occurs and instances where it does not. For example, the phrase "optionally substituted alkylene" means that an alkylene moiety may or may not be substituted and that the description includes both unsubstituted alkylene and alkylene where there is substitution.

A "heterogeneous" catalyst as used herein refers to a catalyst which is supported on a carrier, typically although not necessarily a substrate comprised of an inorganic, solid, particulate porous material such as silicon and/or aluminum oxide.

A "homogeneous" catalyst as used herein refers to a catalyst which is not supported but is simply admixed with the initial monomeric components in a suitable solvent.

The term "multimodal molecular weight distribution" as used herein, and as alluded to above, refers to a polymer composition having two or more molecular weight distributions, as may be determined, for example, by the appearance of two or more peaks in a gel permeation chromatogram. Unless otherwise specified herein, the term "multimodal" is intended to encompass the term "bimodal." Polymer compositions having a "multimodal" molecular weight distribution can be generated using a multimolecular metallocene catalyst in which polymerization takes place at different propagation rates at different active sites within the catalyst structure, or wherein the different active sites give rise to different termination rates, and/or wherein the different active sites have different responses to $H_2$ (or other chain transfer agents). While the term multimodality" generally refers to a multimodal molecular weight distribution, it should be emphasized that a polymer composition can also be "multimodal" with respect to compositional distribution, tacticity distribution, long-chain branching distribution, or the like.

As used herein all reference to the Periodic Table of the Elements and groups thereof is to the version of the table published by the Handbook of Chemistry and Physics, CRC Press, 1995, which uses the IUPAC system for naming groups.

The Novel Catalysts:

The catalysts of the invention are represented by the formula $B(Z)_q$ as shown in structure (I)

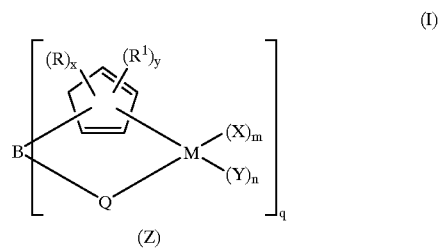

wherein B, Z, Q, M, X, Y, R, $R^1$, x, y, m and n are as defined previously.

B, as noted above, is a covalent bridging group which is comprised of a hydrocarbyl radical optionally containing a Group IVB element, a Group VB element, or both. The bridging group is capable of binding $n_{max}$ substituents through single covalent bonds; $n_{max}$ in turn determines q, the number of Z substituents present in the complex. That is, q is an integer in the range of 2 to $q_{max}$, wherein $q_{max}$ is equal to $\frac{1}{2}n_{max}$ when $n_{max}$ is an even number, and $\frac{1}{2}(n_{max}^-)$ when $n_{max}$ is an odd number. Thus, when $n_{max}$ is 6, up to three Z groups may be present; when $n_{max}$ is 5, one or two Z groups may be present; when $n_{max}$ is 4, again, the maximum number of Z groups is 2. Preferred B groups are $C_1$–$C_{12}$ hydrocarbyl radicals optionally containing a Group IVB element and/or a Group VB element, and particularly preferred B groups are $C_1$–$C_6$ hydrocarbyl groups, e.g., ethylene, dimethylethylene, propylene, etc., and silicon.

The cyclopentadienyl moiety, as shown, is optionally substituted with R and $R^1$ groups. Specifically, the integers x and y are independently 0, 1, 2, 3 or 4, with the proviso that the sum of x and y cannot exceed 4; preferably, x and y are independently 0, 1 or 2, and most preferably are 0 or 1. R and $R^1$ can be halogen, $C_1$–$C_{24}$ hydrocarbyl, either unsubstituted or substituted with one or more halogen atoms, lower alkyl groups and/or Group IVB elements. Alternatively, when an R and an $R^1$ substituent are both present, and ortho to each other on the cyclopentadienyl ring, they may together form a five- or six-membered cyclic structure. This cyclic structure may be unsubstituted or substituted with a halogen or $C_1$–$C_{24}$ hydrocarbyl group as explained above. Preferred R and $R^1$ substituents are halogen and $C_1$–$C_{12}$ alkyl; complexes wherein R and $R^1$ are ortho to each other and linked to form a cyclopentadienyl or indenyl group, either unsubstituted or substituted with halogen and/or lower alkyl moieties, are also preferred. Particularly preferred R and $R^1$ groups are halogen and lower alkyl; complexes wherein R and $R^1$ are ortho to each other and linked to form a cyclopentadienyl ring optionally substituted with a lower alkyl group are also particularly preferred.

Q is cyclopentadienyl, indenyl, fluorenyl, indolyl or aminoboratobenzyl, and may be unsubstituted or substituted with R and/or $R^1$ substituents as above. Alternatively, Q is $J(R^2)_{z-2}$ wherein J is an element with a coordination number of three from Group VB or an element with a coordination number of two from Group VIB, $R^2$ is selected from the group consisting of hydrogen, $C_1$–$C_{24}$ hydrocarbyl, $C_1$–$C_{24}$ hydrocarbyl substituted with one or more, typically one to twelve, halogen atoms, and $C_1$–$C_{24}$ alkoxy, and z is the coordination number of J. In addition, Q substituents on different Z groups may be linked through a $C_1$–$C_{24}$ hydrocarbylene bridge. Typically, although not necessarily, such a linkage is between different $R^2$ groups. Preferred Q substituents are cyclopentadienyl, indenyl, fluorenyl, aminoboratobenzyl or $J(R^2)_{z-2}$ wherein J is nitrogen, phosphorus, oxygen or sulfur, and $R^2$ is $C_1$–$C_2$ alkyl optionally substituted with one or more, typically one to six, halogen atoms. Particularly preferred Q groups are $NR^2$ moieties wherein $R^2$ is lower alkyl or phenyl.

M is a Group IIIA element, a Group IVA element, a Group VA element, a lanthanide, or an actinide. The preferred Group IIIA element is boron. Preferred Group IVA elements are Zr, Hf and Ti, with Zr particularly preferred.

X is hydride, halide, alkoxy, amido, or substituted or unsubstituted $C_1$–$C_{24}$ hydrocarbyl; if substituted, the substituents are electron-withdrawing groups such as a halogen atom, an alkoxy group, or the like, or the substituents may be a Group IVB element. If two or more X moieties are present in the complex, they may be the same or different. When two or more X substituents are present, any two may together form an alkylidene olefin (i.e., $=CR_2$ wherein R is hydrogen or hydrocarbyl, typically lower alkyl), acetylene, or a five- or six-membered cyclic hydrocarbyl group. Preferred X moieties are hydride, amido, $C_1$–$C_2$ alkyl, and $C_1$–$C_2$ alkyl substituted with one or more halogen and/or alkoxy groups, typically one to six such groups, and $C_1$–$C_2$ alkyl substituted with a Group IVB element. Particularly preferred X substituents are hydride, amido and lower alkyl.

The integer "m" defines the number of X substituents bound to the element M, and is 1, 2, 3 or 4. Preferably, m is 1 or 2. When M is boron, m, clearly, cannot exceed 1.

Y is a neutral Lewis base, preferably diethylether, tetrahydrofuran, dimethylaniline, aniline, trimethylphosphine, or n-butylamine. Diethylether and tetrahydrofuran are most preferred.

The integer "n" defines the number of Y substituents bound to the element M, and is 0, 1, 2 or 3. Preferably n is 0 or 1. When M is boron, m is 1, as noted above, and n is necessarily 0. When M is a Group IVB element, the sum of m and n cannot, clearly, exceed 2.

The number of Z groups bound to B is shown in the structure of formula (I) as q, which is in turn defined by "$n_{max}$" as explained above. In the preferred complexes herein, q is 2 or 3, and is most typically 2. The Z groups bound to B may be the same or different. However, it is preferred that the active sites in the catalyst complex be different and chemically distinct, such that two of the metal atoms M are different, or, when all of the metal atoms in the complex are the same, the substituents bound to one are different from those bound to another. When the Z groups are different such that the metallocene contains two distinct and chemically different active sites, the catalyst may then be used to prepare bimodal or multimodal polymers as discussed elsewhere herein.

Examples of specific metallocene catalysts within the purview of the invention include, but are not limited to, the following:

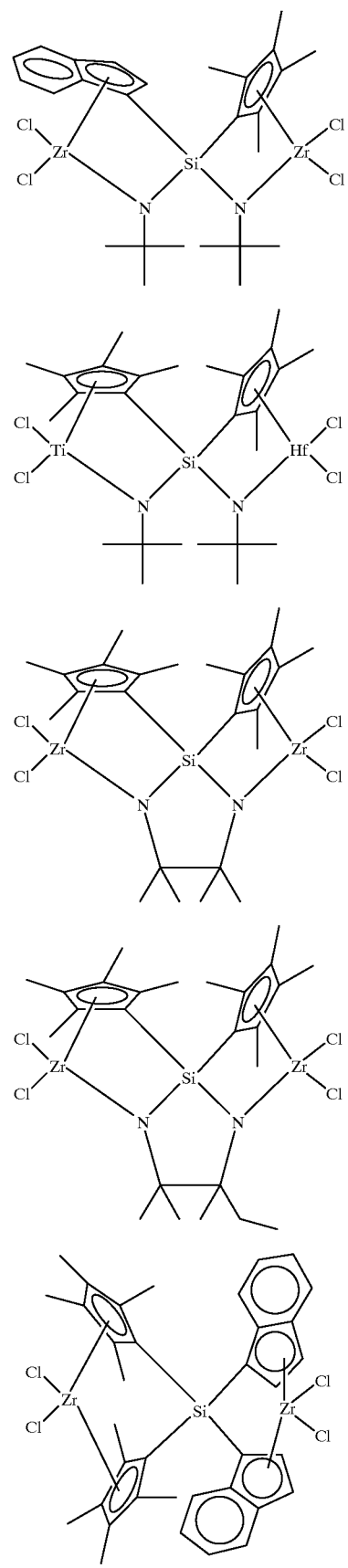

-continued
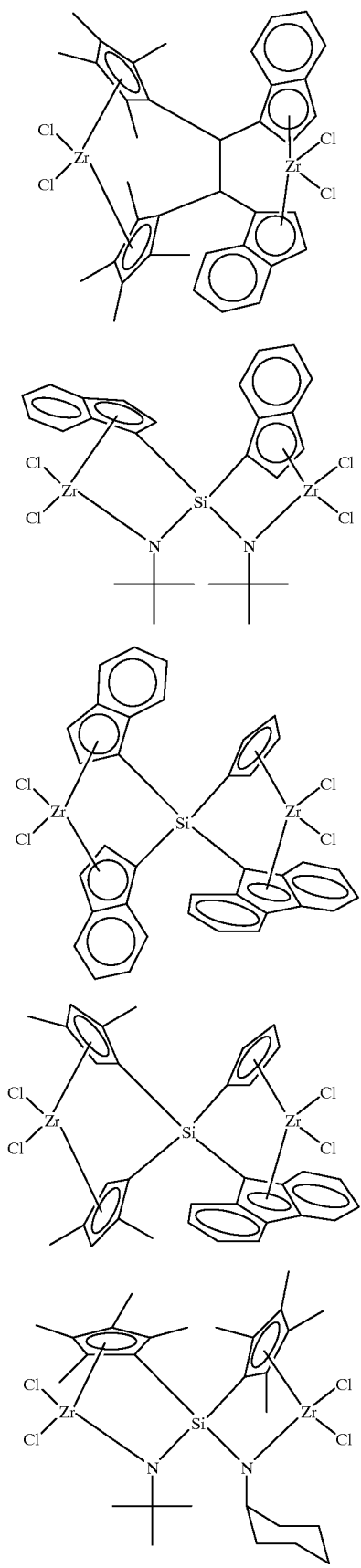
-continued
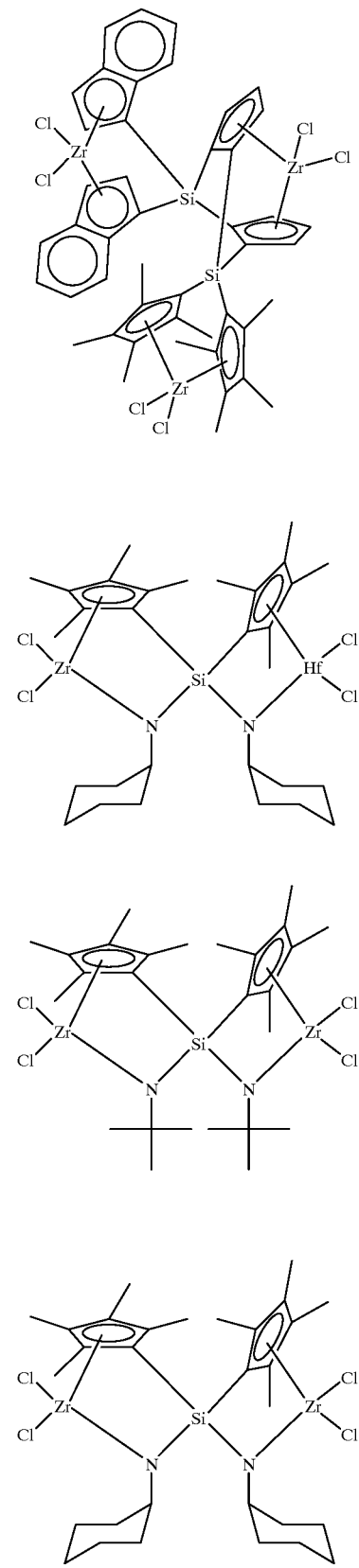

-continued
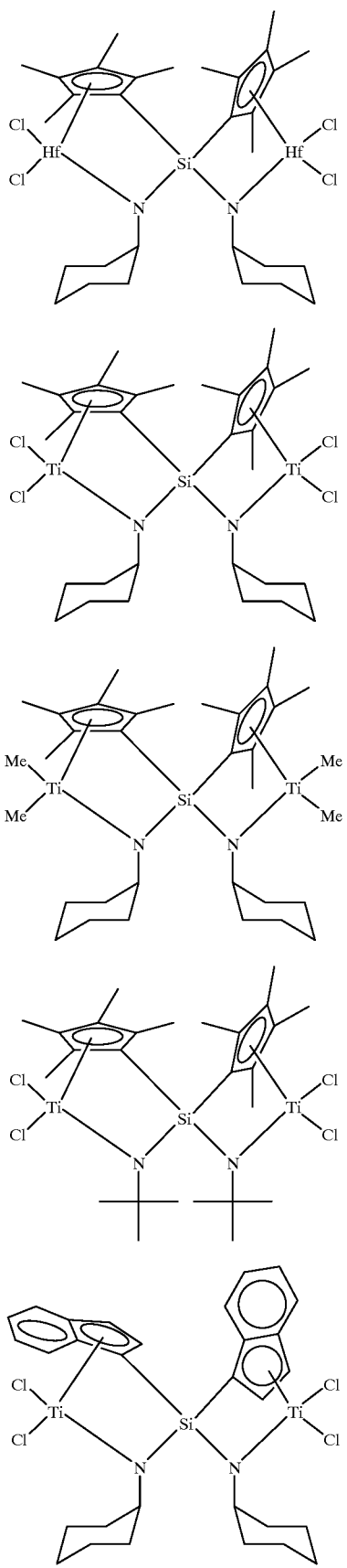
-continued
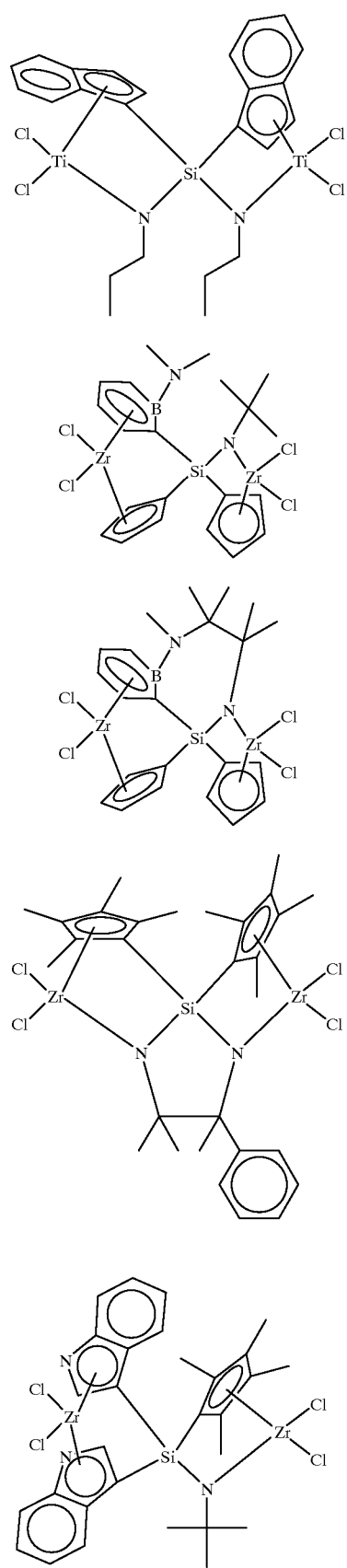

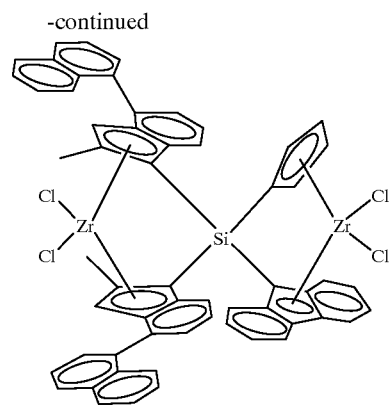

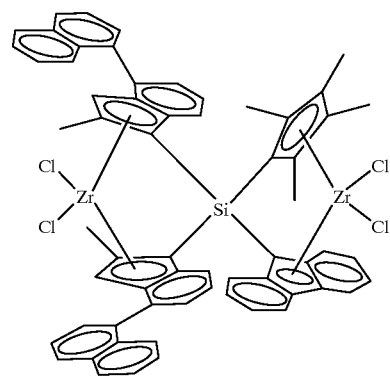

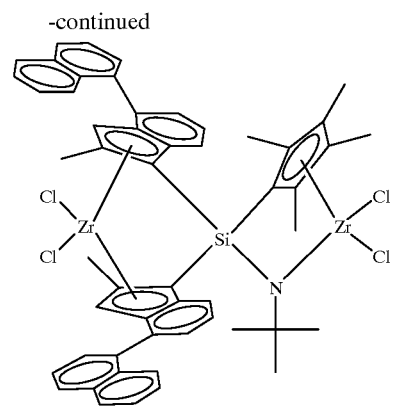

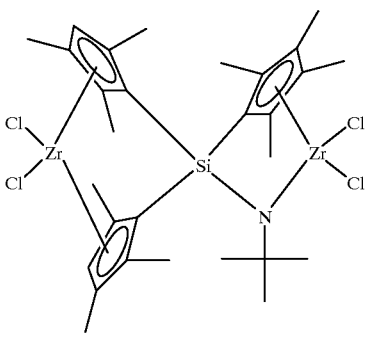

In addition, Table 1 illustrates representative substituents in a typical metallocene catalyst herein:

TABLE 1

| B | Ar* | Q | X | Y | M | Q |
|---|---|---|---|---|---|---|
| silyl | cyclopentadienyl | t-butylamide | hydride | diethylether | zirconium | 2 |
| disilyl | methylcyclopentadienyl | phenylamido | methyl | tetrahydrofuran | hatnium | 3 |
| germanyl | 1,2-dimethylcyclopentadienyl | p-n-butylphenylamido | ethyl | dimethylaniline | titanium | 4 |
| ammonium | 1,3-dimethylcyclopentadienyl | cyclohexylamido | phenyl | aniline | | |
| phosphonium | indenyl | perflurophenylamido | u-propyl | trimethylphosphine | | |
| \Si—O—Si/ | 1,2-diethylcyclopentadienyl | n-butylamido | isopropyt | n-butylamine | | |
| \C/ | tetramethylcyclopentadienyl | methylamido | n-butyl | | | |
| \C=C/ | ethylcyclopentadienyl | ethylamido | amyl | | | |
| \CH—CH/ | | | | | | |
| \CH—CH₂—CH/ | n-butylcyclopentadienyl | n-propylamido | isoamyl | | | |
| \CH—C—CH₃ | cyclohexylmethylcyclopentadienyl | isopropylamido | hexyl | | | |

TABLE 1-continued

| B | Ar* | Q | X | Y | M | Q |
|---|-----|---|---|---|---|---|
| ⟩CH—CH(H)(CH₃)—CH⟨ | n-octylcyclopentadienyl | ben#iamido | isobutyl | | | |
| ⟩CH=C(CH₃)—CH⟨ | β-phenylpropylcyclopentadienyl | 1-butylphosphido | heptyl | | | |
| | tetrahydroindenyl | ethylphosphido | octyl | | | |
| | propylcyclopentaadienyl | phenylphosphido | nonyl | | | |
| | :-butylcyciopentadienyl | cyclohexylphosphido | decyl | | | |
| | benzylcyciopentadienyl | oxo | cetyl | | | |
| | 1,2-dichlorocyclopentadienyl | methoxide | ethylidene | | | |
| | 1,3-dichlorocyclopentadienyl | sulfido | methylidene | | | |
| | methylindenyl | ethoxide | propylidene | | | |
| | trifluoromethylcyciopentadienyl | methylthio | chloro | | | |
| | 1,2-difluorocyclopentadienyl | ethylthio | | | | |
| | fluorenyl | cyclopentadienyl | | | | |
| | methylfluorenyl | indenyl | | | | |
| | octahydrofluorenyl | fluorenyl | | | | |
| | indolyl | aminoboratobenzyl | | | | |
| | methylindolyl | | | | | |
| | 2-methyl-4-phenyl indenyl | | | | | |
| | 2-methyl-4-napthyl indenyl | | | | | |
| | 2-methyl-4-butyl indenyl | | | | | |

In Table 1, "Ar" represents the substituent

as shown in the structure of Formula (I).

Preparation of the Catalyst System:

The novel metallocenes of the invention are used in conjunction with a conventional catalyst activator as will be appreciated by those skilled in the art. Suitable catalyst activators include metal alkyls, hydrides, alkylhydrides, and alkylhalides, such as alkyllithium compounds, dialkylzinc compounds, trialkyl boron compounds, trialkylaluminum compounds, alkylaluminum halides and hydrides, and tetraalkylgermanium compounds. Specific examples of useful activators include n-butyllithium, diethylzinc, di-n-propylzinc, triethylboron, triethyl-luminum, triisobutylaluminum, tri-n-hexylaluminum, ethylaluminum dichloride, dibromide and dihydride, isobutyl aluminum dichloride, dibromide and dihydride, di-n-propylaluminum chloride, bromide and hydride, diisobutyl-aluminum chloride, bromide and hydride, ethyl-luminum sesquichloride, methylaluminoxane ("MAO"), hexaisobutyl-aluminoxane, tetraiso-utyl luminoxane, polymethylaluminoxane, tri-n-octylaluminum, tetramethyl-germanium, and the like. Other activators which are typically referred to as ionic cocatalysts may also be used; such compounds include, for example, $(C_6H_6)_3^+$, $C_6H-NH_2CH_3^+$, and tetra(pentafluoro-phenyl)boron. Mixtures of activators may, if desired, be used.

For liquid phase or slurry polymerization, the catalyst and activator are generally mixed in the presence of inert diluents such as, for example, aliphatic or aromatic hydrocarbons, e.g., liquified ethane, propane, butane, isobutane, n-butane, n-hexane, isooctane, cyclohexane, methylcyclohexane, cyclopentane, methylcyclopentane, cycloheptane, methylcycloheptane, benzene, ethylbenzene, toluene, xylene, kerosene, Isopar® M, Isopar® E, and mixtures thereof. Liquid olefins or the like which serve as the monomers or comonomers in the polymerization process may also serve as the diluent; such olefins include, for example, ethylene, propylene, butene, 1-hexene and the like. The amount of catalyst in the diluent will generally be in the range of about 0.01 to 1.0 mmoles/liter, with activator added such that the ratio of catalyst to activator is in the range of from about 10:1 to 1:2000, preferably in the range of from about 1:1 to about 1:200, on a molar basis.

Various additives may be incorporated into the mixture; particularly preferred additives are neutral Lewis bases such as amines, anilines and the like, which can accelerate the rate of polymerization.

Preparation of the catalyst/activator/diluent mixture is normally carried out under anhydrous conditions in the absence of oxygen, at temperatures in the range of from about −90° C. to about 300° C., preferably in the range of from about −10° C. to about 200° C.

The catalyst, activator and diluent are added to a suitable reaction vessel, in any order, although, as noted above, the catalyst and activator are usually mixed in the diluent and the mixture thus prepared then added to the reactor.

Use in Polymerization:

The novel catalysts are used to prepare polymeric compositions using conventional polymerization techniques known to those skilled in the art and/or described in the pertinent literature. The monomer(s), catalyst and catalyst activator are contacted at a suitable temperature at reduced, elevated or atmospheric pressure, under an inert atmosphere, for a time effective to produce the desired polymer composition. The catalyst may be used as is or supported on a suitable support. In one embodiment, the novel metallocene compounds are used as homogeneous catalysts, i.e., as unsupported catalysts, in a gas phase or liquid phase polymerization process. A solvent may, if desired, be employed. The reaction may be conducted under solution or slurry conditions, in a suspension using a perfluorinated hydrocarbon or similar liquid, in the gas phase, or in a solid phase powder polymerization.

Liquid phase polymerization generally involves contacting the monomer or monomers with the catalyst/activator mixture in the polymerization diluent, and allowing reaction to occur under polymerization conditions, i.e., for a time and at a temperature sufficient to produce the desired polymer product. Polymerization may be conducted under an inert atmosphere such as nitrogen, argon, or the like, or may be conducted under vacuum. Preferably, polymerization is conducted in an atmosphere wherein the partial pressure of reacting monomer is maximized. Liquid phase polymerization may be carried out at reduced, elevated or atmospheric pressures. In the absence of added solvent, i.e., when the olefinic monomer serves as the diluent, elevated pressures are preferred. Typically, high pressure polymerization in the absence of solvent is carried out at temperatures in the range of about 180° C. to about 300° C., preferably in the range of about 250° C. to about 270° C., and at pressures on the order of 200 to 20,000 atm, typically in the range of about 1000 to 3000 atm. When solvent is added, polymerization is generally conducted at temperatures in the range of about 150° C. to about 300° C., preferably in the range of about 220° C. to about 250° C., and at pressures on the order of 10 to 2000 atm.

Polymerization may also take place in the gas phase, e.g., in a fluidized or stirred bed reactor, using temperatures in the range of approximately 60° C. to 120° C. and pressures in the range of approximately 10 to 1000 atm.

The monomer or comonomers used are addition polymerizable monomers containing one or more degrees of unsaturation. Olefinic or vinyl monomers are preferred, and particularly preferred monomers are a-olefins having from about 2 to about 20 carbon atoms, such as, for example, linear or branched olefins including ethylene, propylene, 1-butene, 3-methyl-1-butene, 1,3-butadiene, 1-pentene, 4-methyl-1-pentene, 1-hexene, 4-methyl-1-hexene, 1,4-hexadiene, 1,5-hexadiene, 1-octene, 1,6-octadiene, 1-nonene, 1-decene, 1,4-dodecadiene, 1-hexadecene, 1-octadecene, and mixtures thereof. Cyclic olefins and diolefins may also be used; such compounds include, for example, cyclopentene, 3-vinylcyclohexene, norbornene, 5-vinyl-2-norbornene, 5-ethylidene-2-norbornene, dicyclopentadiene, 4-vinylbenzocyclo-butane, tetracyclododecene, dimethano-octahydronaphthalene, and 7-octenyl-9-borabicyclo-(3,3)nonane. Aromatic monomers which may be polymerized using the novel metallocenes include styrene, o-methylstyrene, m-methylstyrene, p-methylstyrene, p-tert-butylstyrene, m-chlorostyrene, p-chlorostyrene, p-fluorostyrene, indene, 4-vinylbiphenyl, acenaphthalene, vinylfluorene, vinylanthracene, vinylphenanthrene, vinylpyrene and vinylchrisene. Other monomers which may be polymerized using the present catalysts include methylmethacrylate, ethylacrylate, vinyl silane, phenyl silane, trimethylallyl silane, acrylonitrile, maleimide, vinyl chloride, vinylidene chloride, tetrafluoroethylene, isobutylene, carbon monoxide, acrylic acid, 2-ethylhexylacrylate, methacrylonitrile and methacrylic acid.

In gas and slurry phase polymerizations, the catalyst is used in a heterogeneous process, i.e., supported on an inert inorganic substrate. Conventional materials can be used for the support, and are typically particulate, porous materials; examples include oxides of silicon and aluminum, or halides of magnesium and aluminum. Particularly preferred supports from a commercial standpoint are silicon dioxide and magnesium dichloride.

The polymeric product resulting from the aforementioned reaction may be recovered by filtration or other suitable techniques. If desired, additives and adjuvants may be incorporated into the polymer composition prior to, during, or following polymerization; such compounds include, for example, pigments, antioxidants, lubricants and plasticizers.

With catalysts having two or more distinct and different active sites, polymer compositions are prepared that are bimodal or multimodal in nature, typically, but not necessarily, having a multimodal molecular weight distribution. As explained above, the present catalysts may be synthesized so as to contain two or more active sites at which propagation rates differ, or which have different temperature sensitivities and/or $H_2$ responsiveness. In this way, the type and degree of multimodality in the polymeric product can be controlled as desired. Bimodal or multimodal polymer compositions are useful insofar as rheological behavior, mechanical strength and elasticity can be improved relative to corresponding compositions which are not multimodal.

Catalyst Synthesis:

The catalysts of the invention are synthesized using any one of several techniques. In general, the catalysts may be prepared using relatively simple and straightforward synthetic processes which enable precise control of the final metallocene structure and the active sites contained therein.

One suitable synthesis involves the use of a halogenated compound $B(Hal)_{2q}$ as a starting material (wherein B and q are as defined earlier herein and "Hal" represents a halogen atom). The compound is contacted with an alkali metal salt of an aromatic compound Ar, containing one to three cyclopentadienyl rings, either substituted or unsubstituted, to provide an intermediate $ArqB(Hal)_q$. (When it is desired that the end product contain different aromatic groups, successive reaction with different aromatic salts is carried out, i.e., $B(Hal)_{2q}$ is first reacted with an alkali metal salt of a first aromatic species Ar1, then with an alkali metal salt of a second aromatic species Ar2, and the like.) This intermediate is then used to prepare a ligand $Ar_qB[J(R^2)_{z-2}H]_q$ wherein J, $R^2$ and z are as defined previously, by reaction with an alkali metal salt of $J(R^2)_{z-2}H$. (Again, for an end product to contain different $J(R^2)_{z-2}$ species, successive reaction is carried out with alkali metal salts of different $J(R^2)_{z-2}H$ groups.) The ligand is deprotonated and then reacted with a halogenated metal compound $M(Hal)_y$, wherein y represents the number of halogen atoms corresponding to the oxidation state of M. In such a case, the metal atoms in the complex will be identical to one another.

In an alternative method, a starting material $B(Hal)_4$ is caused to react with an alkali metal salt of an aromatic compound Ar containing one, two or three cyclopentadiene rings each optionally substituted with x "R" substituents and y "$R^1$" substituents, to give an intermediate having the formula $Ar_2B(Hal)_2$. This intermediate is then caused to react with a bridging compound comprising a $C_1$–$C_2$ linear or branched alkylene linker L substituted with two primary amine substituents, to provide a ligand $Ar_2BL_2$. As above, the ligand is deprotonated and then successively reacted with first and second halogenated metal compounds $M(Hal)_y$, wherein the metal atoms in each of the metal compounds are different, to provide a metallocene catalyst having the structure of formula (I), wherein the metal atoms in each Z substituent are different.

For end products wherein "Q" is other than $J(R^2)_{z-2}$, a similar procedure is carried out, i.e., alkali metal salts of compounds having the general structure Q-H are used in place of alkali metal salts of $J(R^2)_{z-2}$.

Alternative transmetalation techniques are also possible, as will be appreciated by those skilled in the art. For example, Huttenhofer et al., "Substituted Silastannatetrahydro-s-indacenes as Cyclopentadienyl Transfer Agents in the Synthesis of Silanediyl-Bridged Zirconocene Complexes," *Organometallics* 15:4816–4822 (1996), describes a method for preparing metallocenes using substituted silastannatetrahydro-s-indacenes as cyclopentadienyl transfer agents. The Huttenhofer et al. and other methods can be used herein as well.

EXPERIMENTAL

The following examples are put forth so as to provide those of ordinary skill in the art with a complete disclosure and description of how to prepare and use the metallocene catalysts of the invention. Efforts have been made to ensure accuracy with respect to numbers (e.g., amounts, temperature, etc.) but some errors and deviations should be accounted for. Unless indicated otherwise, parts are parts by weight, temperature is in 0° C. and pressure is at or near atmospheric.

All patents, patent applications, journal articles and other references mentioned herein are incorporated by reference in their entireties.

Examples 1 through 9 describe methods for synthesizing various metallocene catalysts; Example 10 describes a procedure for using the catalysts in the preparation of polyethylene; and Example 11 describes the procedure used to evaluate the bimodality of the polymer composition prepared using the catalyst of Example 4.

All procedures were performed under airless conditions. All reagents were purchased from Aldrich (Milwaukee, Wis.) except where noted, all solvents were purchased from Mallinckrodt, and all gases from Liquid Carbonic. In each case, the highest purity material available was purchased. All solvents were redistilled from appropriate purification reagents prior to use. All gases were further purified by passing through deoxygenation and dehydration columns prior to use. All products were characterized by NMR.

Example 1

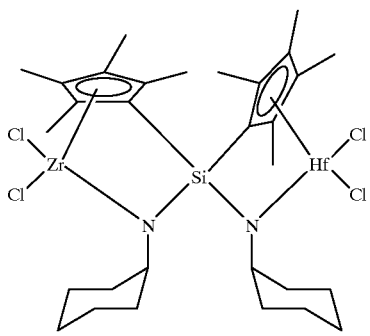

The catalyst shown was prepared as follows:

Tetramethyl cyclopentadiene (4.7 g) was dissolved in 102 ML THF and cooled to −78° C. n-Butyllithium (18.2 mL of 2.2M in hexane) was added dropwise. The mixture was allowed to warm to room temperature and stirred for 1 h. The resulting suspension was then cooled to −30° C. and 2.25 mL of $SiCl_4$ was added over 10 minutes. The mixture was allowed to warm to room temperature to give a colorless solution. The solution was then stirred at room temperature overnight. The solution was then filtered and concentrated to dryness. The solid was then extracted with pentane and filtered. The pentane was removed to give a colorless solid (6.20 g of bis-tetramethylcyclopentadienyl silicon dichloride). (Analytically pure samples could be obtained by recrystallizing from a concentrated pentane solution.)

Bis-tetramethyl cyclopentadienyl silicon dichloride (2.40 g) was then dissolved in 45 mL THF. To this solution lithium cyclohexylamide (1.49 g in portions) was added. The solution was stirred overnight and the solvents then removed. The solid was extracted with pentane, filtered, and the pentane removed. Yield: 3.30 g of light yellow bis cyclohexylamido bis-tetra-methyl cyclopentadienyl silane.

Bis-cyclohexylamido bis-tetramethylcyclopentadienyl silane (3.29 g) was dissolved in 70 mL of $Et_2O$ and cooled to 0° C. n-Butyllithium (3.6 mL of 10 M in hexane) was added slowly. The mixture was allowed to warm to room temperature and stirred overnight. The solvents were removed to yield a yellow solid. The yellow solid was slurried in pentane and filtered. The solid was washed three times with pentane to give 2.30 g of an off-white solid

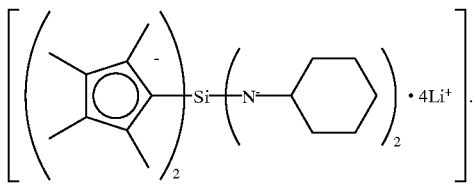

Zirconium tetrachloride (560 mg) and hafnium tetrachloride (770 mg) were slurried in 65 mL diethyl ether. To that slurry was added 1.18 g of the off-white solid prepared above (gradually, over a 15 minute period). The mixture was diluted with 10 mL of diethyl ether (to wash the solid addition funnel). The mixture was allowed to stir for 18 h. The solvent was then removed. The solid was extracted with 20 mL toluene and filtered. The toluene was removed to yield 1.96 g of a pale yellow powder. NMR indicated the expected mixture of products: the Zr-Zr, Zr-Hf and Hf-Hf dimetallated products.

Example 2

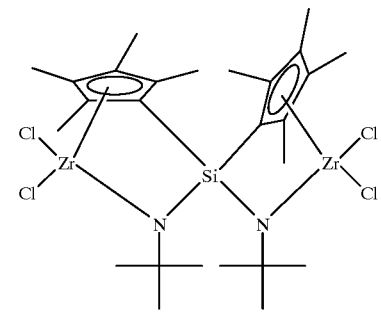

The catalyst shown was prepared as follows:

Bis-tetramethylcyclopentadienyl silicon dichloride was prepared as described in Example 1. Lithium-t-butylamide was slurried in 50 mL diethyl ether. Bis-tetramethyl cyclopentadienyl silicon dichloride (1.88 g) was added slowly. The mixture was allowed to stir overnight. The solvent was removed and the mixture extracted with pentane and filtered. Removal of pentane gave a yellow oil. The yellow oil was dissolved in 100 mL diethyl ether and cooled to 0° C. n-Butyllithium (3.0 mL of 10M in hexane) was added. The reaction was allowed to warm to room temperature and stirred overnight. The solvent was removed, and the remaining solid was slurried in pentane and filtered to give 0.70 g of colorless solid

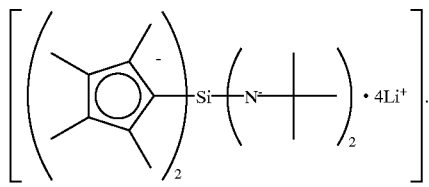

Zirconium tetrachloride (744 mg) was suspended in 60 mL diethyl ether. The 700 mg of colorless solid prepared above was added slowly to the reaction mixture. The solid addition funnel was then washed with 10 mL of diethyl ether which was added to the reaction mixture. The mixture was allowed to stir overnight and the solvent was then removed. The solid was extracted with toluene and then filtered. The toluene was removed to give 1.06 g of a golden colored solid.

Example 3

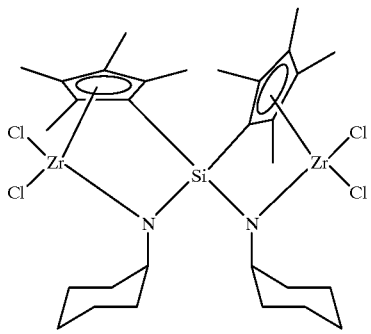

The catalyst shown was prepared as follows:

The ligand was prepared as in Example 1.

Zirconium tetrachloride (932 mg) was slurried in 70 mL diethyl ether. To that slurry was added slowly over 20 minutes 981 mg of

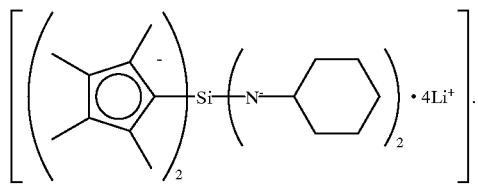

The reaction mixture was stirred for 24 h. The solvent was removed and the solid extracted with toluene. The toluene solution was filtered and the solvent removed to isolate 1.44 g of a light yellow crystalline solid.

Example 4

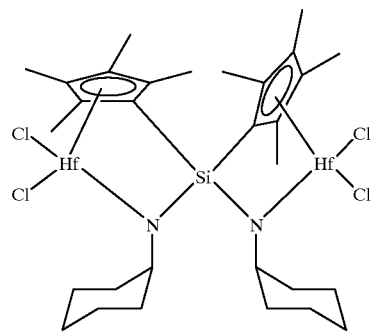

The catalyst shown was prepared as follows:

The ligand was prepared as in Example 1.

Hafnium tetrachloride was slurried in 70 mL diethyl ether. To that slurry was added slowly over 10 min 0.98 g of

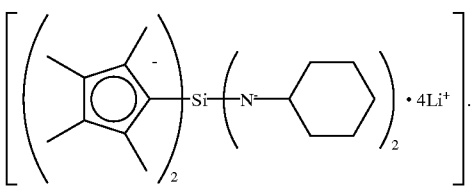

The mixture was allowed to stir for 24 h. The solvent was then removed, and the remaining solid was extracted with toluene. The toluene was removed to isolate a light yellow solid (1.74 g).

Example 5

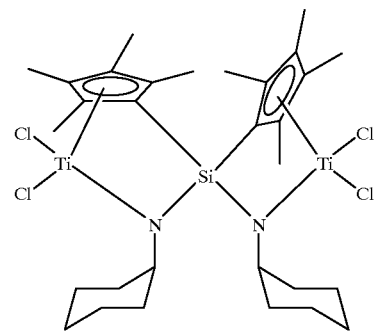

The catalyst shown was prepared as follows: The ligand was prepared as in Example 1. TiCl$_3$·3THF was dissolved in 60 mL THF and 736 mg of the ligand

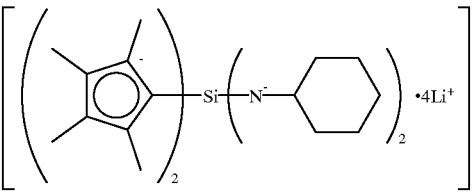

was added. The mixture was allowed to stir for ½ hour giving a purple solution. To that solution 473 mg of AgCl was added. The solution was allowed to stir for 1 h. The solvent was evaporated from the red-brown mixture, and the resulting solid was extracted with pentane and filtered. The solution was then concentrated and cooled to crystallize the reddish yellow product. Repeated concentrations and crystallizations allowed the recovery of several crops of the product (0.60 g combined).

An alternative synthesis of this catalyst is to slurry 1.34 g of TiCl₄·2THF in toluene (70 mL). To this mixture 0.88 g of the ligand

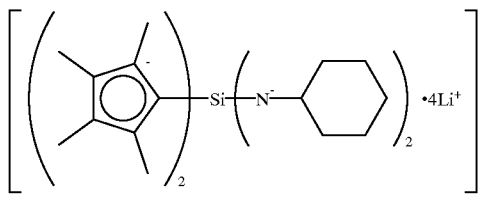

was added slowly. The reaction mixture turned brown quickly. The mixture was allowed to stir for 4 days and then filtered. The toluene was removed, and the resulting solid was extracted in pentane and filtered. The pentane was removed to give a reddish-yellow solid.

Example 6

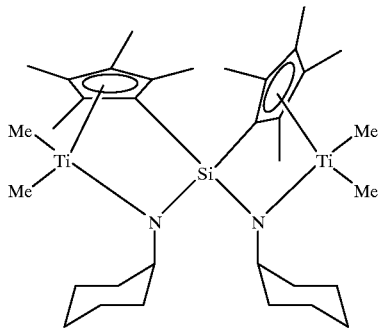

The catalyst shown was prepared as follows:

The catalyst prepared by the first method of Example 5 was used as the starting material in this example.

The catalyst of Example 5 (0.49 g) was dissolved in THF and cooled to −30° C.

CH₃MgCl (0.93 mL, 3M in THF) was added slowly. The reaction was allowed to warm to room temperature and stirred for 1 h. The solvent was removed and the solid extracted with pentane. The pentane solution was filtered and the solvent removed to yield 0.32 g of brown solid.

Example 7

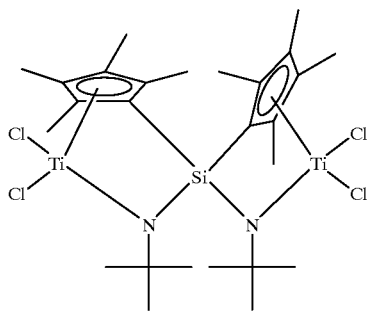

The catalyst shown was prepared as follows:
The ligand

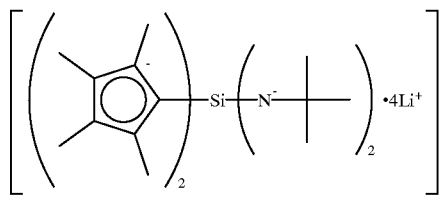

was prepared as in Example 2.

TiCl₃·3THF (1.12g) was slurried in 50 mL of THF. The ligand (0.66 g) was slowly added to this reaction mixture. The deep purple mixture was stirred for 1.5 h and then 0.50g of AgCl was added. The mixture was allowed to continue to stir for 3 h at which time it turned reddish yellow. The mixture was filtered and the solvent removed. The solid was redissolved in toluene, filtered, and the toluene removed. This solid was then slurried in pentane, filtered, and the pentane removed to give a small amount of reddish yellow product.

Example 8

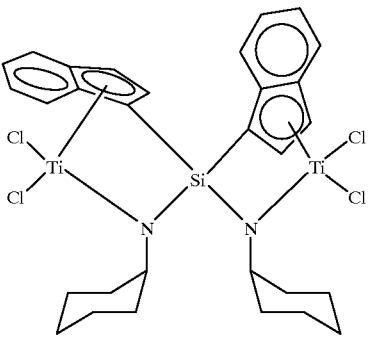

The catalyst shown was prepared as follows:
Indene (5.81 g) was dissolved in 25 nL of toluene and 20 mL of 3M EtMgBr in diethyl ether was added. The mixture was slowly heated until the ether was distilled off. Then the mixture was heated at toluene reflux for 5.5 h. The mixture was allowed to cool and the toluene removed under vacuum. The solid was dried at 80–90° C. for ½ h. The solid was washed with hexanes. The indenyl Grignard was then slurried in 200 mL diethyl ether and cooled to −20° C. to −30° C. SiCl₄ (2.9 mL in 100 mL Et₂0) was added slowly over~½ h. The suspension was allowed to warm to room temperature and then heated to reflux. The mixture was held at reflux overnight and then allowed to cool. The Et₂0 was removed in vacuum. The solid was stirred in hexanes for 2 h and filtered. The hexanes were removed by vacuum to give 6.63 g of light yellow solid: dichloro,diindenyl silane.

Dichloro, diindenyl silane (6.45 g) was slurried in 20 mL hexanes and 10 mL diethyl ether. The mixture was cooled to 0° C. and 9.2 mL of cyclohexylamine in 10 mL hexanes was added slowly. The mixture was heated to reflux for 1 h, cooled and filtered. The solvent was removed to give di(cyclohexylamino)diindenyl silane as a tan solid (7.60 g).

Di(cyclohexylamino)diindenyl silane (7.60 g) was dissolved in 140 mL of diethyl ether. n-Butyllithium (8.0 mL of 10 M in hexane) was added. The mixture was allowed to stir for 2 days. The diethyl ether was removed. The solid was extracted with pentane and filtered. The pentane was removed yielding a colorless solid (8.03 g):

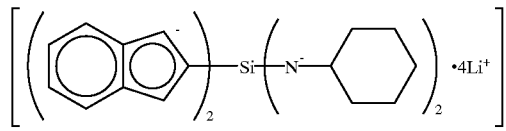

A slurry in toluene (60 mL) was made of 0.96 g of the ligand shown and 1.34 g of TiCl₄·2THF. The mixture was allowed to stir for 6 days. The slurry was filtered and the toluene removed to give a red-brown solid of the catalyst (0.84 g).

Example 9

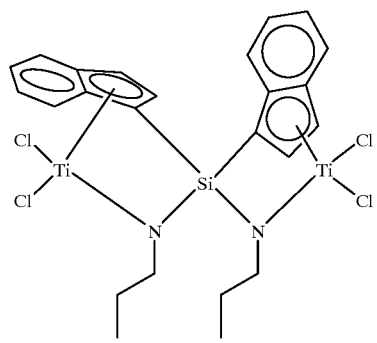

The catalyst shown was prepared as follows:

Dichloro, diindenyl silane was prepared as in Example 8. n-Propylamine (0.5 mL) was dissolved in 25 mL of hexanes and cooled to 0° C. Dichloro, diindenylsilane (28 g) in 25 mL of hexanes was slowly added. The addition funnel was washed with 5 mL of diethyl ether which was added to the reaction mixture. The reaction mixture was heated at reflux for 1 h. The mixture was allowed to cool and filtered. The solvent was removed to give 7.53 g of tan oil.

The tan oil (7.45 g) prepared above

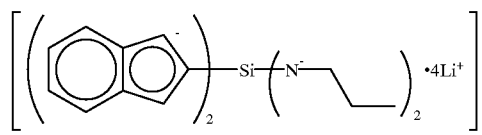

was dissolved in a mixture of 55 mL pentane and 15 mL diethyl ether. n-Butyllithium (8.2 mL of 10 M in hexanes) was added dropwise. The reaction was highly exothermic. The suspension was refluxed for 2 h and 10 addition mL of diethyl ether added. The mixture was filtered and the solid was washed with a 1:1 mixture of diethyl ether and pentane. 7.05 g of

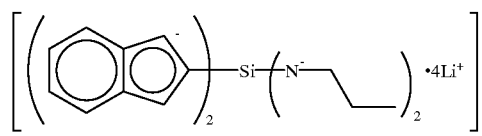

were collected.

TiCl₄·2THF (1.01 g) and 1.20 g of the ligand shown were mixed and 70 mL of toluene added. The reaction mixture turned reddish brown. The mixture was allowed to stir for 24 h. Then additional TiCl₄·2THF was dissolved in 25 mL toluene and added to the reaction mixture. The mixture was allowed to stir for 5 days. The mixture was filtered and the solvent removed. The solid was extracted with pentane and filtered. The pentane was removed to give 1.46 g of brown solid.

Example 10

The metallocene compounds prepared in Examples 1 through 9 were used as polymerization catalysts in the preparation of polyethylene ("PE"). The amount of catalyst used and reaction temperature are in Table 2. Standard ethylene polymerization conditions were used, as follows: Polymerizations were conducted in a 300 mL autoclave reactor. Methyl aluminoxane (MAO) was used as co-catalyst with total Al/M ratio equal to 1000 (with the exception of the comparison polymerization with Cp₂ZrCl₂ which was run with Al/M=2000). Prior to initiation of polymerization, the reactors were loaded with 160 mL of toluene and the MAO. The reactors were heated to the desired reaction temperature and pressurized with ethylene to 40 psig. The reactors were configured to maintain the set pressure and temperature during the polymerization reaction. The reaction was initiated by injection of the catalyst. The reactions were run for 30 minutes and terminated by injection of acidified methanol (2% HCl). The polymer was removed from the reactor and washed with additional acidified methanol, aqueous NaHCO₃, water and acetone. The polymer was dried in a vacuum oven overnight.

Results are set forth in Table 2:

TABLE 2

| Catalyst Example # | Amount of Catalyst Used | Reaction Temperature | Catalyst Activity PE: metallocene | PE: metal | Amount of PE Isolated |
|---|---|---|---|---|---|
| 1 | 3.4 μmol; 3 mg | 70° C. | 3,080 | 10,000 | 4.62 g. |
| 2 | 4.5 μmol: 3.3 mg | 70° C. | 2,691 | 10,850 | 4.44 g. |
| 3 | 2.5 μmol: 2.0 mg | r.t. | 2,440 | 10,517 | 2.44 g. |
| 3 | 2.5 μmol: 2.0 mg | 70° C. | 2,700 | 11,638 | 2.70 g. |
| 3 | 3.5 μmol: 2.8 mg | 105° C. | 3,757 | 16,194 | 5.26 g. |
| 4 | 3.1 μmol: 3.0 mg | r.t. | 193 | 521 | 0.29 g. |
| 4 | 3.1 μmol: 3.0 mg | 70° C. | 1,733 | 4,672 | 2.60 g. |
| 4 | 3.1 μmol: 3.0 mg | 115° C. | 1,573 | 4,241 | 2.36 g. |
| 4 | 3.1 μmol: 3.0 mg | 70° C., 20 min | — | — | 2.22 g. |
| 5 | 4.2 μmol: 3.0 mg | 70° C. | 733 | 5,353 | 1.10 g. |
| 5 | 2.1 μmol: 1.5 mg | 70° C. | 320 | 2,336 | 0.24 g. |
| 5 | 2.8 μmol: 2.0 mg | 70° C. | 260 | 1,898 | 0.26 g. |
| 5 | 1.4 μmol: 1.0 mg | 70° C. | 840 | 6,131 | 0.42 g. |
| 5 | 2.8 μmol: 2.0 mg | r.t. | 1280 | 9,343 | 1.28 g. |
| 6 | <8 μmol | r.t. | — | — | little |
| 7 | 4.6 μmol: 3.0 mg | 70° C. | — | — | 0 |
| $Cp_2ZrCl_2$ (standard) | 5.0 μmol, 1.5 mg | 70° C. | 11,267 | 36,112 | 8.45 g |
| 8 | 1.4 μmol, 1.0 mg | 70° C. | 560; 720 | 3972; 5106 | 0.28 g., 0.36 g. |
| 9 | 1.6 μmol, 1.0 mg | 70° C. | 480+ | 3057 | 0.24 g |

Example 11

The polyethylene composition produced using the procedure of Example 10 and the catalyst of Example 4 was evaluated using gel permeation chromatography. FIG. 1 shows a typical bimodal distribution obtained. Other catalysts as described herein are expected to provide multimodal polymer compositions as well.

What is claimed is:

1. A supported metallocene catalyst containing more than one active site, having the structure $B(Z)_q$ of structural formula (I)

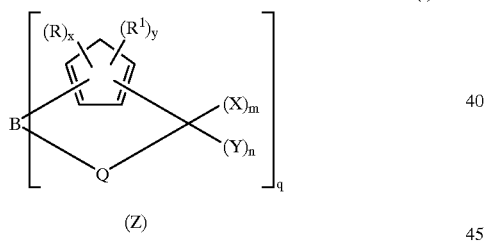

(I)

wherein:

B is a covalent bridging group comprising carbyl, silyl, disilyl, germanyl, ammonium, phosphonium,

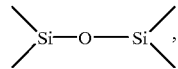

or a $C_1-C_{24}$ hydrocarbyl radical optionally containing a Group IVB element, a Group VB element, or both a Group IVB element and a Group VB element, and is capable of binding up to $n_{max}$ substituents through single covalent bonds, where $n_{max}$ is at least 4;

R and $R^1$ are independently selected from the group consisting of halogen, $C_1-C_{24}$ hydrocarbyl, $C_1-C_{24}$ hydrocarbyl substituted with one or more halogen atoms, and $C_1-C_{24}$ hydrocarbyl-substituted Group IVB elements, x is 0, 1, 2, 3 or 4, and y is 0, 1, 2, 3 or 4, with the proviso that the sum of x and y cannot exceed 4, or, when R and $R^1$ are ortho to each other and x and y are each 1 or greater, R and $R^1$ can together form a five- or six-membered cyclic structure optionally substituted with one to four substituents selected from the group consisting of halogen, $C_1-C_{24}$ hydrocarbyl, $C_1-C_{24}$ hydrocarbyl substituted with one or more halogen atoms, and $C_1-C_{24}$ hydrocarbyl-substituted Group IVB elements;

Q is cyclopentadienyl, indenyl, fluorenyl, indolyl or aminoboratobenzyl, optionally substituted with one or more R and $R^1$ substituents as above, or Q is $J(R^2)_{z-2}$ wherein J is an element with a coordination number of three from Group VB or an element with a coordination number of two from Group VIB, $R^2$ is selected from the group consisting of hydrogen, $C_1-C_{24}$ hydrocarbyl, $C_1-C_{24}$ hydrocarbyl substituted with one or more halogen atoms, and $C_1-C_{24}$ alkoxy, and z is the coordination number of J, and further wherein Q substituents on different Z groups may be linked through a $C_1-C_{24}$ hydrocarbylene bridge;

M is a Group IIIA element, a Group IVA element, a Group VA element, a lanthanide, or an actinide;

X is selected from the group consisting of hydride, halide, alkoxy, amido, $C_1-C_{24}$ hydrocarbyl, $C_1-C_{24}$ hydrocarbyl radicals substituted with one or more electron-withdrawing groups, and $C_1-C_{24}$ hydrocarbyl-substituted Group IVB elements, or, when two or more X substituents are present, they may together form an alkylidene olefin, acetylene, or a five- or six-membered cyclic hydrocarbyl group;

Y is a neutral Lewis base, m is 1, 2, 3 or 4, and n is 0, 1, 2 or 3, with the proviso that if M is a Group IIIA element, m is 1 and n is 0, and with the further proviso that if M is a Group IVA element, the sum of m and n does not exceed 2;

if $n_{max}$ is 4 or 5, then q is 2, and if $n_{max}$ is greater than 5, then q is an integer in the range of 2 to $q_{max}$, wherein $q_{max}$ is equal to ½ $n_{max}$ when $n_{max}$ is an even number, and ½($n_{max}$-1) when $n_{max}$ is an odd number, with the proviso that when q is 2 and the M elements in the two Z groups are the same, Q is necessarily $J(R^2)_{z-2}$; and at least two of the Z substituents bound to B are different, wherein the catalyst is supported on an inert inorganic support material.

2. The catalyst of claim 1, wherein the support material is comprised of a porous, particulate solid.

3. The catalyst of claim 2, wherein the support material is comprised of silicon dioxide.

4. The catalyst of claim 2, wherein the support material is comprised of aluminum oxide.

5. A supported metallocene catalyst containing more than one active site, having the structure $B(Z)_q$ of structural formula (I)

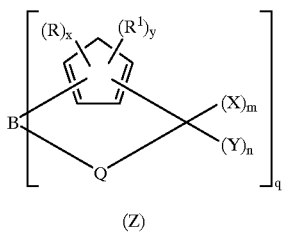

(I)

wherein:

B is a covalent bridging group comprising carbyl, silyl, disilyl, germanyl, ammonium, phosphonium,

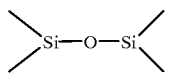

or a $C_1$–$C_{24}$ hydrocarbyl radical optionally containing a Group IVB element, a Group VB element, or both a Group IVB element and a Group VB element, and is capable of binding up to $n_{max}$ substituents through single covalent bonds, where $n_{max}$ is at least 4;

R and $R^1$ are independently selected from the group consisting of halogen, $C_1$–$C_{24}$ hydrocarbyl, $C_1$–$C_{24}$ hydrocarbyl substituted with one or more halogen atoms, and $C_1$–$C_{24}$ hydrocarbyl-substituted Group IVB elements, x is 0, 1, 2, 3 or 4, and y is 0, 1, 2, 3 or 4, with the proviso that the sum of x and y cannot exceed 4, or, when R and $R^1$ are ortho to each other and x and y are each 1 or greater, R and $R^1$ can together form a five- or six-membered cyclic structure optionally substituted with one to four substituents selected from the group consisting of halogen, $C_1$–$C_{24}$ hydrocarbyl, $C_1$–$C_{24}$ hydrocarbyl substituted with one or more halogen atoms, and $C_1$–$C_{24}$ hydrocarbyl-substituted Group IVB elements;

Q is cyclopentadienyl, indenyl, fluorenyl, indolyl or aminoboratobenzyl, optionally substituted with one or more R and $R^1$ substituents as above, or Q is $J(R^2)_{z-2}$ wherein J is an element with a coordination number of three from Group VB or an element with a coordination number of two from Group VIB, $R^2$ is selected from the group consisting of hydrogen, $C_1$–$C_{24}$ hydrocarbyl, $C_1$–$C_{24}$ hydrocarbyl substituted with one or more halogen atoms, and $C_1$–$C_{24}$ alkoxy, and z is the coordination number of J, and further wherein Q substituents on different Z groups may be linked through a $C_1$–$C_{24}$ hydrocarbylene bridge;

M is a Group IVA element, a Group VA element, a lanthanide, or an actinide;

two X substituents together form an alkylidene olefin, acetylene, or a five- or six-membered cyclic hydrocarbyl group, and if additional X substituents are present, they are selected from the group consisting of hydride, halide, alkoxy, amido, $C_1$–$C_{24}$ hydrocarbyl, $C_1$–$C_{24}$ hydrocarbyl radicals substituted with one or more electron-withdrawing groups, and $C_1$–$C_{24}$ hydrocarbyl-substituted Group IVB elements;

Y is a neutral Lewis base;

m is 2, 3 or 4, and n is 0, 1, 2 or 3, with the proviso that if M is a Group IVA element, m is 2 and n is 0;

if $n_{max}$ is 4 or 5, then q is 2, and if $n_{max}$ is greater than 5, then q is an integer in the range of 2 to $q_{max}$, wherein $q_{max}$ is equal to $\frac{1}{2}n_{max}$ when $n_{max}$ is an even number, and $\frac{1}{2}(n_{max}-1)$ when $n_{max}$ is an odd number, with the proviso that when q is 2 and the M elements in the two Z groups are the same, Q is necessarily $J(R^2)_{z-2}$; and the Z substituents bound to B may be the same or different, wherein the catalyst is supported on an inert inorganic support material.

6. The catalyst of claim 5, wherein the support material is comprised of a porous, particulate solid.

7. The catalyst of claim 6, wherein the support material is comprised of silicon dioxide.

8. The catalyst of claim 6, wherein the support material is comprised of aluminum oxide.

9. A supported metallocene catalyst containing more than one active site, having the structure $B(Z)_q$ of structural formula (I)

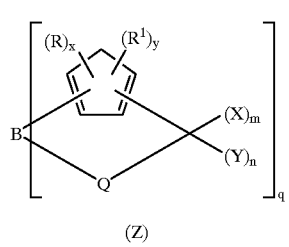

(I)

wherein:

B is a covalent bridging group comprising carbyl, silyl, disilyl, germanyl, ammonium, phosphonium,

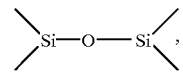

or a $C_1$–$C_{24}$ hydrocarbyl radical optionally containing a Group IVB element, a Group VB element, or both a Group IVB element and a Group VB element, and is capable of binding up to $n_{max}$ substituents through single covalent bonds, where $n_{max}$ is at least 4;

R and $R^1$ are independently selected from the group consisting of halogen, $C_1$–$C_{24}$ hydrocarbyl, $C_1$–$C_{24}$ hydrocarbyl substituted with one or more halogen atoms, and $C_1$–$C_{24}$ hydrocarbyl-substituted Group IVB elements, x is 0, 1, 2, 3 or 4, and y is 0, 1, 2, 3 or 4, with the proviso that the sum of x and y cannot exceed 4, or, when R and $R^1$ are ortho to each other and x and y are each 1 or greater, R and $R^1$ they can together form a five- or six-membered cyclic structure optionally substituted with one to four substituents selected from the group consisting of halogen, $C_1$–$C_{24}$ hydrocarbyl, $C_1$–$C_{24}$ hydrocarbyl substituted with one or more halogen atoms, and $C_1$–$C_{24}$ hydrocarbyl-substituted Group IVB elements;

Q is cyclopentadienyl, indenyl, fluorenyl, indolyl or aminoboratobenzyl, optionally substituted with one or more R and $R^1$ substituents as above, or Q is $J(R^2)_{z-2}$ wherein J is an element with a coordination number of three from Group VB or an element with a coordination number of two from Group VIB, $R^2$ is selected from the group consisting of hydrogen, $C_1$–$C_{24}$ hydrocarbyl, $C_1$–$C_{24}$ hydrocarbyl substituted with one or more halogen atoms, and $C_1$–$C_{24}$ alkoxy, and z is the coordination number of J, and further wherein Q substituents on different Z groups are linked through a $C_1$–$C_{24}$ hydrocarbylene bridge;

M is a Group IIIA element, a Group IVA element, a Group VA element, a lanthanide, or an actinide;

X is selected from the group consisting of hydride, halide, alkoxy, amido, $C_1$–$C_{24}$ hydrocarbyl, $C_1$–$C_{24}$ hydrocarbyl radicals substituted with one or more electron-withdrawing groups, and $C_1$–$C_{24}$ hydrocarbyl-substituted Group IVB elements, or, when two or more X substituents are present, they may together form an alkylidene olefin, acetylene, or a five- or six-membered cyclic hydrocarbyl group;

Y is a neutral Lewis base;

m is 1, 2, 3 or 4, and n is 0, 1, 2 or 3, with the proviso that if M is a Group IIIA element, m is 1 and n is 0, and with the further proviso that, if M is a Group IVA element, the sum of m and n does not exceed 2;

if $n_{max}$ is 4 or 5, then q is 2, and if $n_{max}$ is greater than 5, then q is an integer in the range of 2 to $q_{max}$, wherein $q_{max}$ is equal to $\frac{1}{2}n_{max}$ when $n_{max}$ is an even number, and $\frac{1}{2}(n_{max}-1)$ when $n_{max}$ is an odd number, with the proviso that when q is 2 and the M elements in the two Z groups are the same, Q is necessarily $J(R^2)_{z-2}$; and the Z substituents bound to B may be the same or different, wherein the catalyst is supported on an inert, inorganic support material.

10. The catalyst of claim 9, wherein the support material is comprised of a porous, particulate solid.

11. The catalyst of claim 10, wherein the support material is comprised of silicon dioxide.

12. The catalyst of claim 10, wherein the support material is comprised of aluminum oxide.

13. A supported metallocene catalyst having the structure

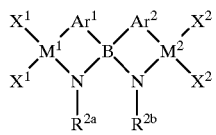

wherein:

B is carbyl, lower alkylene, lower alkenylene or silyl;

$Ar^1$ and $Ar^2$ are independently selected from the group consisting of cyclopentadienyl, indenyl and fluorenyl, optionally substituted with at least one substituent selected from the group consisting of halogen and lower alkyl;

$M^1$ and $M^2$ are independently selected from the group consisting of Zr, Hf and Ti;

the $X^1$ and $X^2$ may be the same of different and are selected from the group consisting of halide, lower alkyl and lower alkoxy; and $R^{2a}$ and $R^{2b}$ are selected from the group consisting of $C_1$ to $C_{12}$ alkyl and phenyl, with the proviso that $R^{2a}$ and $R^{2b}$ are different, wherein the catalyst is supported on an inert inorganic support material.

14. The supported metallocene catalyst of claim 13, wherein B is selected from the group consisting of

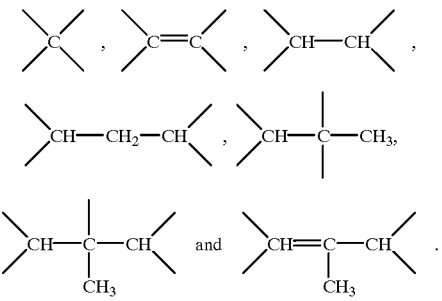

15. The supported metallocene catalyst of claim 14, wherein B is selected from the group consisting of

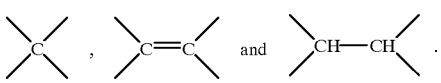

16. The supported metallocene catalyst of claim 15, wherein B is

17. The supported metallocene catalyst of claim 16, wherein B is

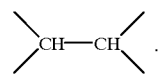

18. The supported metallocene catalyst of claim 13, wherein B is silyl.

19. The supported metallocene catalyst of claim 13, wherein $M^1$ and $M^2$ are different.

20. The supported metallocene catalyst of claim 13, wherein $M^1$ and $M^2$ are the same.

21. The supported metallocene catalyst of claim 13, wherein the $X^1$ and $X^2$ are independently chloro or methyl.

22. The supported metallocene catalyst of claim 21, wherein the $X^1$ are chloro and the $X^2$ are methyl.

23. The supported metallocene catalyst of claim 21, wherein the $X^1$ and $X^2$ are all chloro.

24. The supported metallocene catalyst of claim 21, wherein the $X^1$ and $X^2$ are all methyl.

25. A supported metallocene catalyst having the structure

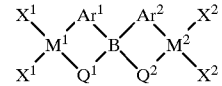

wherein:

B is carbyl, lower alkylene, lower alkenylene or silyl;

$Ar^1$ and $Ar^2$ are independently selected from the group consisting of cyclopentadienyl, indenyl and fluorenyl, optionally substituted with at least one substituent selected from the group consisting of halogen and lower alkyl;

$M^1$ and $M^2$ are independently selected from the group consisting of Zr, Hf and Ti;

the $X^1$ and $X^2$ may be the same of different and are selected from the group consisting of halide, lower alkyl and lower alkoxy; and $Q^1$ and $Q^2$ are selected from the group consisting of cyclopentadienyl, indenyl, fluorenyl, indolyl and aminoboratobenzyl, optionally substituted with at least one substituent selected from the group consisting of halogen and lower alkyl, with the proviso that $Q^1$ and $Q^2$ are different, and with the further provisos that (a) when $M^1(X^1)_2$ is the same as $M^2(X^2)_2$ and $Q^1$ is the same as Ar2, then $Q^2$ and $Ar^1$ must be different, and (b) when $M^1(X^1)_2$ is the same as $M^2(X^2)_2$ and $Q^2$ is the same as $Ar^1$, the $Q^1$ and Ar2 must be different, wherein the catalyst is supported on an inert, inorganic support material.

26. The supported metallocene catalyst of claim 25, wherein B is selected from the group consisting of

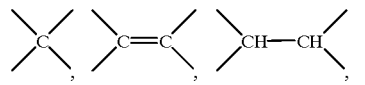

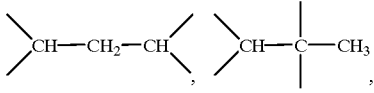

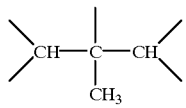

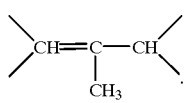

27. The supported metallocene catalyst of claim 26, wherein B is selected from the group consisting of

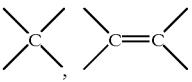

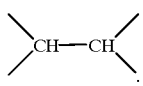

28. The supported metallocene catalyst of claim 27, wherein B is

29. The supported metallocene catalyst of claim 27, wherein B is

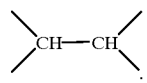

30. The supported metallocene catalyst of claim 13, wherein B is silyl.

31. The supported metallocene catalyst of claim 25, wherein $M^1$ and $M^2$ are different.

32. The supported metallocene catalyst of claim 25, wherein $M^1$ and $M^2$ are the same.

33. The supported metallocene catalyst of claim 25, wherein the $X^1$ and $X^2$ are independently chloro or methyl.

34. The supported metallocene catalyst of claim 33, wherein the $X^1$ are chloro and the $X^2$ are methyl.

35. The supported metallocene catalyst of claim 33, wherein the $X^1$ and $X^2$ are all chloro.

36. The supported metallocene catalyst of claim 33, wherein the $X^1$ and $X^2$ are all methyl.

37. A supported metallocene catalyst having the structure

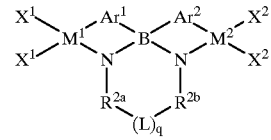

wherein:

B is carbyl, lower alkylene, lower alkenylene or silyl;

$Ar^1$ and $Ar^2$ are independently selected from the group consisting of cyclopentadienyl, indenyl and fluorenyl, optionally substituted with at least one substituent selected from the group consisting of halogen and lower alkyl;

$M^1$ and $M^2$ are independently selected from the group consisting of Zr, Hf and Ti;

the $X^1$ and X2 may be the same of different and are selected from the group consisting of halide, lower alkyl and lower alkoxy; $R^{2a}$ and $R^{2b}$ are independently selected from the group consisting of methylene, phenylethylene, lower alkyl-substituted methylene, di(lower alkyl)-substituted methylene, and methylene substituted with one lower alkyl group and phenyl;

L is methylene optionally substituted with 1 or 2 lower alkyl groups, and q is 0 or 1, wherein the catalyst is supported on an inert, inorganic support material.

38. The supported metallocene catalyst of claim 37, wherein B is selected from the group consisting of

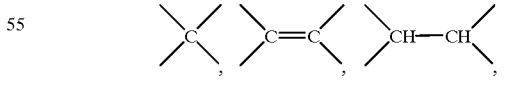

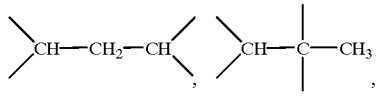

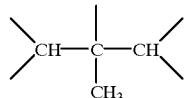

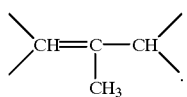

39. The supported metallocene catalyst of claim 38, wherein B is selected from the group consisting of

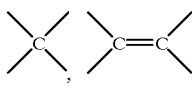

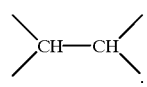

40. The supported metallocene catalyst of claim 39, wherein B is

41. The supported metallocene catalyst of claim 39, wherein B is

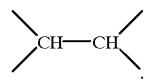

42. The supported metallocene catalyst of claim 37, wherein B is silyl.

43. The supported metallocene catalyst of claim 37, wherein $M^1$ and $M^2$ are different.

44. The supported metallocene catalyst of claim 37, wherein $M^1$ and $M^2$ are the same.

45. The supported metallocene catalyst of claim 37, wherein the $X^1$ and $X^2$ are independently chloro or methyl.

46. The supported metallocene catalyst of claim 45, wherein the $X^1$ are chloro and the $X^2$ are methyl.

47. The supported metallocene catalyst of claim 45, wherein the $X^1$ and $X^2$ are all chloro.

48. The supported metallocene catalyst of claim 45, wherein the $X^1$ and $X^2$ are all methyl.

49. The supported metallocene catalyst of claim 37, wherein q is 0.

50. The supported metallocene catalyst of claim 37, wherein $R^{2a}$ and $R^{2b}$ are independently selected from the group consisting of methylene, methylethylene, dimethylmethylene and methylethylmethylene.

51. The supported metallocene catalyst of claim 50, wherein $R^{2a}$ and $R^2b$ are both dimethylmethylene.

52. The catalyst of claim 13, wherein the support material is comprised of a porous, particulate solid.

53. The catalyst of claim 52, wherein the support material is comprised of silicon dioxide.

54. The catalyst of claim 52, wherein the support material is comprised of aluminum oxide.

55. The catalyst of claim 25, wherein the support material is comprised of a porous, particulate solid.

56. The catalyst of claim 55, wherein the support material is comprised of silicon dioxide.

57. The catalyst of claim 55, wherein the support material is comprised of aluminum oxide.

58. The catalyst of claim 37, wherein the support material is comprised of a porous, particulate solid.

59. The catalyst of claim 58, wherein the support material is comprised of silicon dioxide.

60. The catalyst of claim 58, wherein the support material is comprised of aluminum oxide.

* * * * *